United States Patent [19]

Martin

[11] Patent Number: 4,907,965
[45] Date of Patent: Mar. 13, 1990

[54] ELECTROTHERMAL DENTAL DEBRACKETING TOOL AND METHOD OF REMOVAL

[75] Inventor: Patrick E. Martin, Laguna Beach, Calif.

[73] Assignee: Johnson & Johnson Consumer Products, Inc., New Brunswick, N.J.

[21] Appl. No.: 187,696

[22] Filed: Apr. 29, 1988

[51] Int. Cl.⁴ .................................................. A61C 7/00
[52] U.S. Cl. ......................................................... 433/3
[58] Field of Search .................................. 433/2, 3, 32

[56] References Cited

U.S. PATENT DOCUMENTS 4,455,138 6/1984 Sherdian .................................. 433/3

Primary Examiner—Robert Peshock
Attorney, Agent, or Firm—Paul A. Coletti

[57] ABSTRACT

A heating element is inserted into the archwire slot of the tooth in order to allow the adhesive surface of a dental bracket to become loose. Force is exerted by a pull wire, controlled by a force limiting spring, until the bracket is removed. No harm comes to the patient or the tooth.

15 Claims, 4 Drawing Sheets

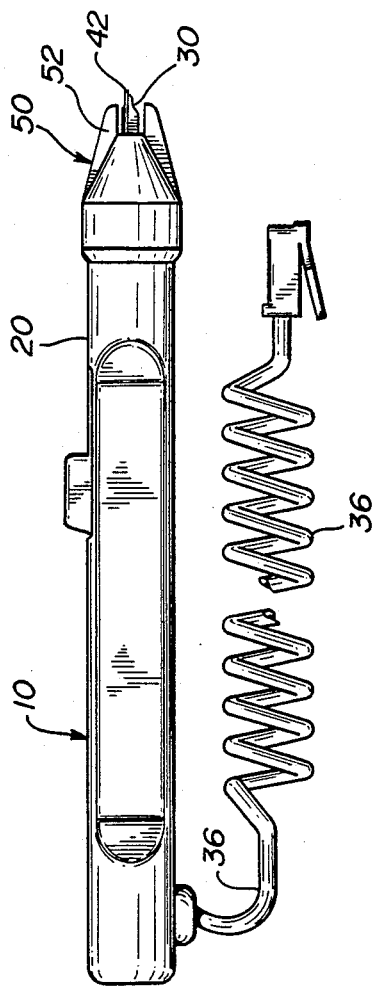
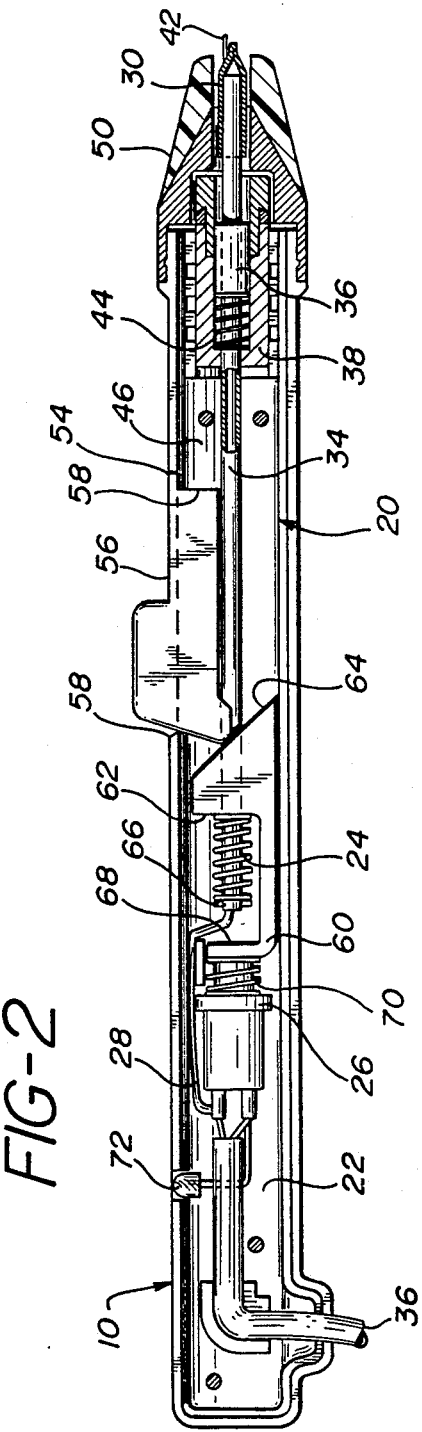
FIG-1
FIG-2

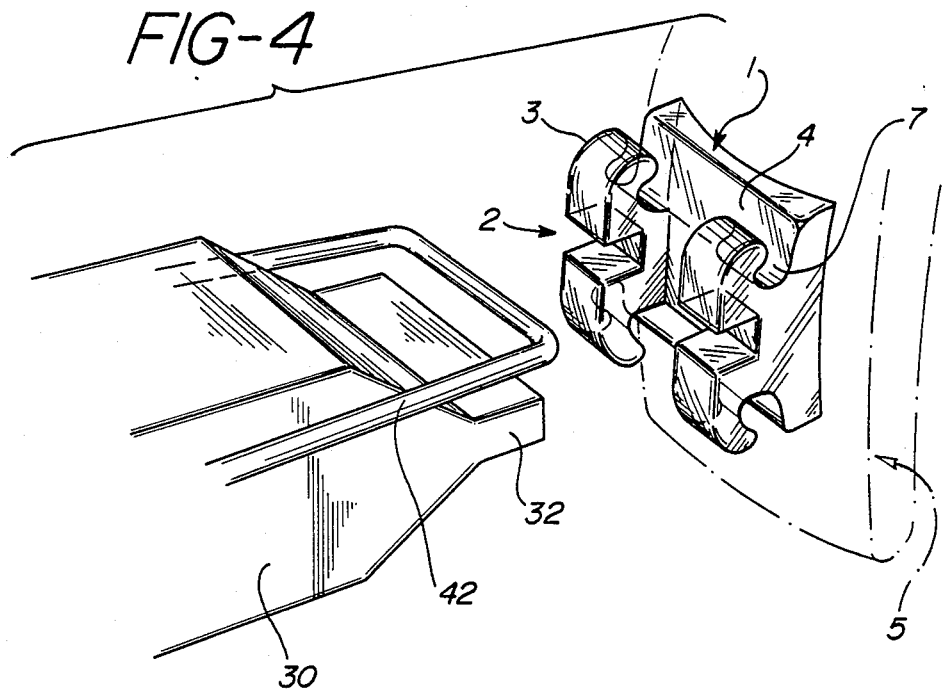
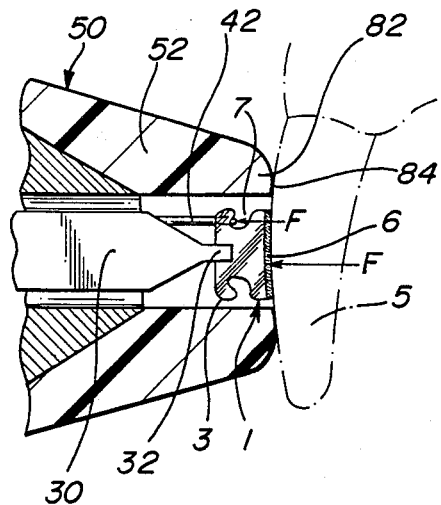

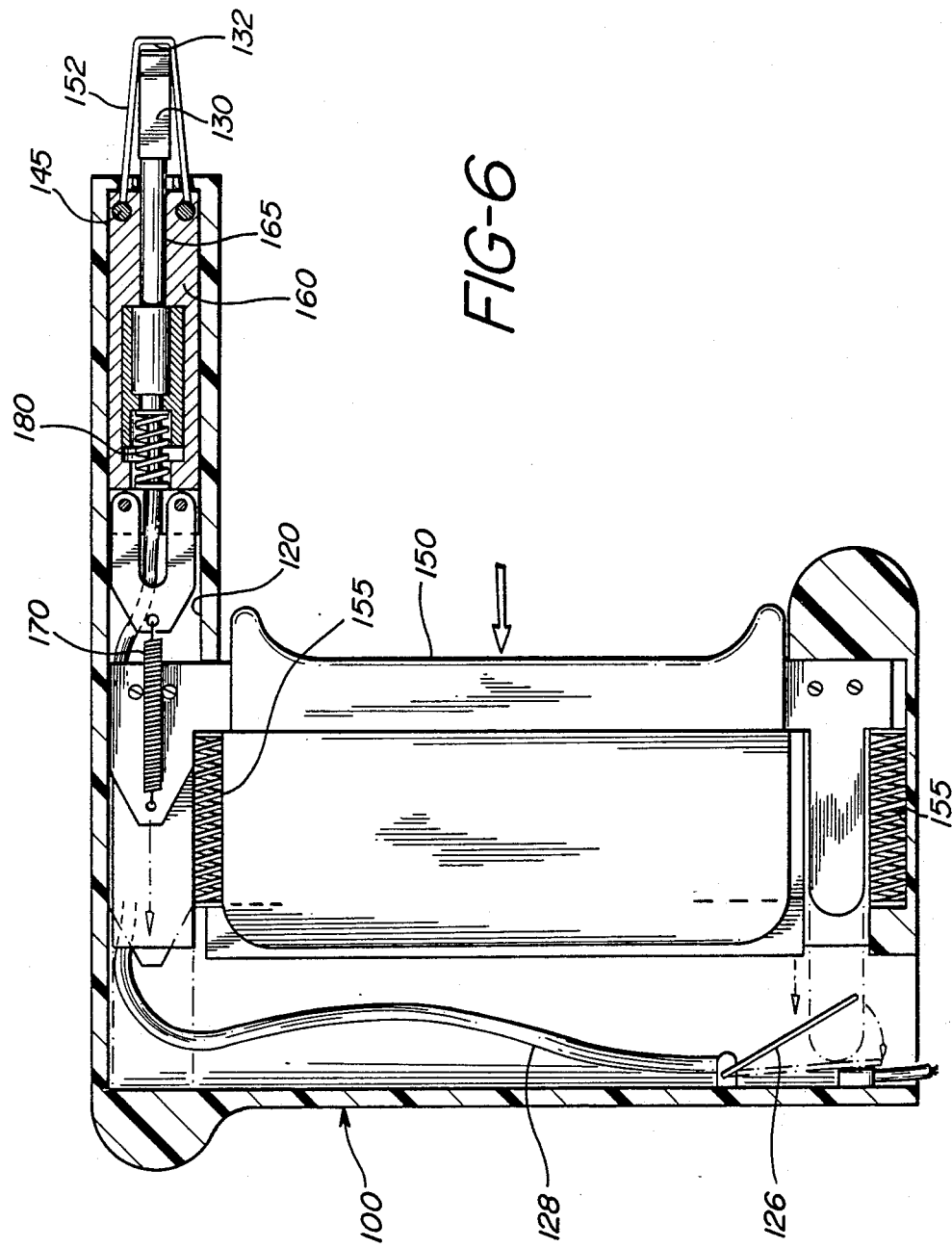

ELECTROTHERMAL DENTAL DEBRACKETING TOOL AND METHOD OF REMOVAL

FIELD OF THE INVENTION

This invention relates generally to a tool and method for the removal of dental brackets. More specifically, this invention relates to a tool and method for the removal of ceramic brackets bonded to teeth. Most specifically, this invention relates to a tool and method for the removal of dental brackets bonded to teeth through the application of heat to the bracket, along with a controlled pulling force, thus removing the bracket when the adhesive bonding forces are loosened.

BACKGROUND OF INVENTION

Historically, dental brackets have been quite easy to remove. That is, metal brackets which are generally bonded to a set of teeth have been removed through the use of dental pliers. After the removal of the archwire from each bracket, the orthodontist merely needed to pry the brackets, as a set, from the teeth. This required some bending of the bracket, but was not seen as a problem, due to the ease of removal. The orthodontist was able to remove the entire set of brackets within a matter of minutes. The brackets, if not extensively damaged, would be repaired and autoclaved for reuse. If beyond repair, the brackets would simply be discarded.

In recent years there has been an increase in the use of ceramic and sapphire brackets. These brackets are generally formed from a fired ceramic or sapphire material, and must be bonded to the tooth. This bonding allows each tooth to individually support a bracket, and the archwire strung through the set of brackets constantly urges the teeth into proper position in the mouth.

Removal of these ceramic and sapphire brackets, however, has proved quite difficult. Early techniques for removal included the prying of the individual dental brackets from the teeth. This posed a significant number of problems. First, the adhesive bonding strength caused the dental bracket to remain on the tooth face long enough so that a torque was transmitted to the root of the tooth. This frequently caused pain to the patient. Second, often the bonding strength of the adhesive was stronger than the shear strength of the bracket. When the bracket was removed by the prying method, the adhesive would often cause part of the bracket to remain on the tooth face. The rest of the bracket would shatter in the patient's mouth. This set of circumstances could prove quite trying. The chips of the dental bracket were usually dispersed, and the part of the dental bracket remaining on the tooth would need to be filed from the tooth face by a diamond-edged wheel.

Diamond cutting provided its own problems. First, many orthodontists are not adequately skilled in the use of a diamond cutting wheel. Second, this procedure can be quite tedious. Without a steady hand, there is the possibility of removal of the dental enamel along with the pieces of bracket and the bonding adhesive.

The final problem caused by prying of the dental brackets was that it could be extremely time consuming. Each tooth could take up to five minutes or more to have the bracket pried and then cleaned. This procedure could take up to one hour for an entire set of brackets, which is considered excessive both by patients and orthodontists.

Attempts were made to change the procedure of removal of dental brackets by the use of heat on the bracket. The early work of Sheridan, which culminated in U.S. Pat. No. 4,455,138, granted Jun. 19, 1984, demonstrated that with the application of heat to the dental bracket, the adhesive bonding the bracket to the tooth face would be loosened. The bracket could then be more easily pulled from the tooth face with a smaller prying force. This would allow quicker and more complete removal of the dental bracket without the need for prying.

The Sheridan device, however, also had significant drawbacks, much like the drawbacks encountered using the prying method. Because there was no control over the amount of force applied by the orthodontist, this force could vary from orthodontist to orthodontist. Thus, even though the bracket was being heated, the orthodontist could pull the bracket in anticipation of the loosening of the adhesive from the bracket. Again, this could potentially cause great pain. It also did not prevent the over-eager orthodontist from cracking or shattering the dental bracket before there was a chance to apply heat to loosen the adhesive.

Also, the Sheridan method had another significant drawback; the pulling force could not be directionally controlled. That is, the pulling force had no corresponding reaction force into the tooth face. Therefore, the orthodontist could twist or pry the tooth and exert a torque on the tooth face. In addition, the orthodontist could pull the tooth in any direction, creating shear on the tooth. This was potentially painful to the patient, and also enhanced the probability of shattering the bracket.

SUMMARY OF THE INVENTION

Therefore, it is an object of the present invention to provide a dental debracketing tool which allows heat to be applied to the bracket while simultaneously exerting a controlled pulling force on the bracket.

It is a further object of the present invention to provide a dental debracketing tool which provides a reaction force near the dental bracket, in order to avoid the creation of any torques or shear forces during debracketing.

It is a further object of the present invention to provide a method whereby a pulling force can simultaneously be exerted on a dental bracket only during the time when heat is applied to the dental bracket, in order to provide for the loosening of the adhesive on the dental bracket.

These and other objects are accomplished in the present invention which provides a dental debracketing tool wherein a heating element is placed within the archwire slot of the dental bracket. Simultaneously, a pull wire is placed between the groove created by the tie wings of the dental bracket and the dental bracket face. A reaction force is provided on the tooth face. A trigger mechanism is activated which applies a pulling force from the pulled wire to the dental bracket. Concurrently with the application of the pulling force, a switch is activated, which allows heat to be applied to the dental bracket. Upon the application of just a sufficient amount of heat to adequately loosen the adhesive bond, the pulling force overcomes the bonding strength of the adhesive and pulls the dental bracket at an approximate right angle to the tooth face.

No pain is felt by the patient because no shearing forces or torques are applied to the dental bracket. In addition, because there is a reaction force, the pull is felt only on the tooth face and not in the area surrounding the tooth. Finally, because there is a constant, although minimal, pulling force exerted on the dental bracket, the bracket is removed at the earliest possible moment upon loosening of the bonding strength of the adhesive. This occurs well before the dental bracket and tooth face have warmed to a significant level to cause any pain to the tooth of the patient.

In addition, the present invention discloses a method for the removal of a dental bracket whereby a pull wire is attached to the tie wing of the bracket, and a heating element is inserted into the archwire slot of the bracket. Thereafter, a switch means activates the heating element within the bracket, and the bracket is heated until the pulling force overcomes the adhesive force bonding the bracket to the tooth.

BRIEF DESCRIPTION OF THE DRAWINGS

The invention will be better understood by reference to the accompanying drawings and the attached detailed description of the present invention, in which:

FIG. 1 is a plan view of a preferred embodiment of the present invention;

FIG. 2 is a cut-away view of FIG. 1.

FIG. 4 is a close-up perspective view of the heating element and puller assembly of the present invention;

FIG. 5 is a cross-sectional view of the heating element and puller assembly in place within a dental bracket; and FIG. 6 is a cross-sectional plan view of an alternate preferred embodiment of the present invention.

DETAILED DESCRIPTION OF THE INVENTION

Figure 3:
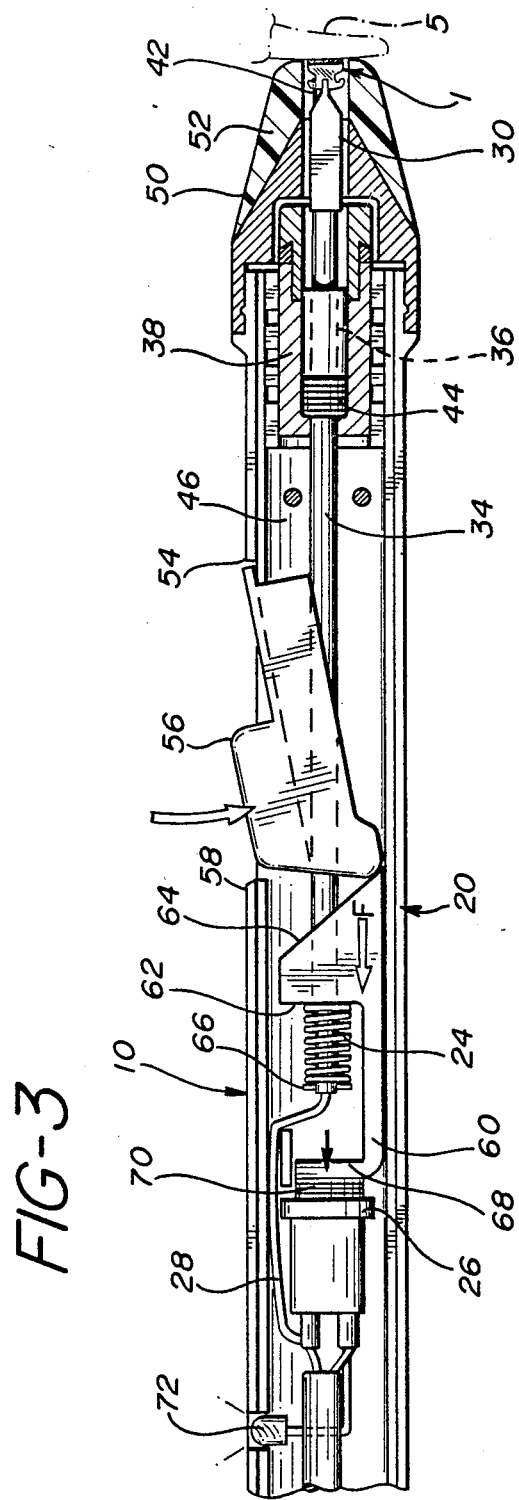
FIG. 3 is a cut-away view of FIG. 1 during operation of a preferred embodiment of the present invention.

Turning now to the above-described drawings, it is seen in FIGS. 1 through 5 that there is disclosed a dental debracketing device 10 for removing a dental bracket 1. The device 10 will be formed from components, such as industrial plastics, having high structural integrity. As best seen in FIG. 4 and FIG. 5, these dental brackets 1 are generally bonded to a tooth 5 by means of an adhesive 6. The adhesive 6 is generally formed from a paste of generally adherent organic compounds, and many are commonly available in the dental market. The dental bracket 1 is generally formed from a ceramic or sapphire material, such as the Starfire ™ Brackets commonly sold by The "A"-Company, La Jolla, Calif. Each of these dental brackets 1 contains an archwire slot 2 formed by the tie wings 3 of the dental bracket. The tie wings 3 also form a groove 7 between the dental bracket face 4 and the tie wings 3.

As seen in FIGS. 1-3, the device 10 will generally consist of a body section 20 into which slides a heating element 30. A puller assembly 40 is attached to the heating element 30. In addition, a nose portion 50 will extend over the combined heating element 30 and puller assembly 40. The heating element 30 and puller assembly 40 will be retractable within the nose portion 50 and the body section 20.

In general, the puller assembly 40 contains a pull wire 42 which can be inserted around the tie wings 3 into the groove 7 created near the dental bracket face 4. This pull wire 42 is attached to the heating element 30 in a manner to allow them to work coordinately with one another. The heating element 30, because it is retractable within the body section 20, can convey a pulling force to the puller assembly 40.

As best seen in FIGS. 4 and 5, the heating element 30, usually formed from brass or any other conductor, contains a slotted end 32. This slotted end 32 fits snugly within the archwire slot 2 of the dental bracket 1. In addition, the heating element 30 is attached to a pen tube 34, as seen in FIG. 3. This generally cylindrical pen tube 34 extends through the hollow tube 22 of the body section. In addition, the heating element 30 has a large cylindrical attachment 36 to which the pen tube 34 is attached. This cylindrical attachment 36 is seated within a sliding block 38, which is a generally cylindrical yoke. The sliding block 38 allows third spring 44 to control the motion of the puller assembly 40. In addition, the pen tube 34 is seated within a set of bushings 46. These bushings 46 control the motion of the pen tube 34 within the hollow tube 22 of the body section 20.

The pen tube 34 extends to the rear of the body section 20 and is attached at the rear to a first spring 24. This first spring 24 is a force limiting compression spring, which contacts a ramp 60 at its other end. This ramp 60 has a generally perpendicular face 62 and a generally angular face 64. The perpendicular face 62 comes into contact with the end of the first spring 24. At the end where the first spring 24 is attached to the pen tube 22, there is a limiting bar 66, which prevents relaxation of the spring during pulling.

The ramp 60 also contains a elbow shaped extension 68 which is attached to a second spring 70. This second spring 70 contacts a control switch 26. The control switch connects an electrical line 28 from the heating element 30 to the power source by means of a cord 36. There is an indicating light 72 also attached to the control switch 26.

Further examining the body section 20, there is a slotted opening 58 in which is seated a finger control 56. The finger control 56 is hinged to the body section 20 at a hinge 54. When turning to the nose portion 50, there is also seen a tubular section 52 from which is generally formed from a pair of prongs 82 which culminate in flat faces 84. It will be these faces 84 which are attached to the tooth 5.

In operation of the electrothermal debracketing device 10, therefore, the pull wire 42 is first attached to the groove 7 of the dental bracket 1. This is accomplished by movement of the pull wire 42 in relation to heating element 30, while heating element 30 moves within the sliding block 38. It is to be noted that third spring 44 generally urges the large cylindrical attachment 36 within the nose portion 50, so that the heating element 30 and pull wire 42 are exposed in order to enable their attachment to the dental bracket from outside the prongs 82. Once the pull wire 42 is attached to the tie wing 3 within the groove 7, the heating element 30 can be attached or placed within the archwire slot 2 of the dental bracket 1 at the slotted end 32 of the heating element 30.

At this point the device is ready for operation. The operator then presses on the finger control 56, which contacts and activates the ramp 60. This causes the ramp 60 to move in a direction away from the heating element 30 as seen in FIG. 3. The movement of the ramp 60 also causes the second spring 70 to compress so that the control switch 26 is activated, applying electrical energy to the heating element 30 in order to heat the dental bracket 1. At this point, the indicating light 72 is also activated.

The movement of the ramp 60 away from the heating element 30 also causes the compression of the first spring 24. When this first spring 24 is compressed, it causes a pulling force F to be exerted on the limiting bar 66 connected to the pen tube 34. This pulling force F is transferred to the pen tube 34, and is then exerted on the heating element 30, to which the pull wire 42 is attached. Thus, the pull wire will exert the same force F on the tie wings 3 of the dental bracket 1, as seen in FIG. 5.

The heating of the dental bracket 1 by the heating element 30 causes the adhesive 6 to lose most of its bonding strength. It is to be recognized that the loosening of the adhesive bonding strength need not be accomplished by electrothermal resistance heating; rather any effective breaking of the bonding strength, such as laser energy, ultraviolet light, infrared heating and the like, will suffice. When the force F exceeds the adhesive bonding strength, it causes the dental bracket 1 to be removed from the surface of the tooth 5. At that point, the first spring 24 relaxes, pulling the pen tube 34 and the heating element 30 (with the dental bracket 1 attached) away from the tooth 5. This first spring 24 limits the amount of force exerted on the dental bracket 1. That is, the only force exerted on the bracket will be the force F caused by compression. Force exerted by the orthodontist will only be absorbed into the spring force of the first spring 24. This overcomes human interference in the force applied to the dental bracket 1.

Once the dental bracket 1 has been removed, the operator is able to release the grip on the finger control 56 such that the second spring 70 returns to its normal configuration and the control switch 26 is deactivated, thereby removing any electrical energy from the heating element 30 and its slotted end 32. The indicating light 72 will then go off.

A second, more simplified embodiment of the present invention is disclosed in FIG. 6. This second preferred embodiment of the device 100 contains a heating element 130 having a slotted end 132. A sliding block 160 fits within the hollow body section 120 of the device 100. The sliding block 160 is connected by means of a spring 170 to a trigger mechanism 150. The trigger mechanism 150 is forced into position by springs 155.

Attached to the sliding block 160 is a pull wire 152, by pin 145. The heating element 130 is able to move within a hollow chamber 165 in the sliding block 160. The spring 180 is connected to the sliding block 160 at one end, and to the heating element 130 at its other end. Thus, the sliding block 160 and pull wire 152 are moveable relative to the heating element 130 by means of the spring 180. A nose portion not shown, identical to nose portion 50 of the previous embodiment, provides a base to supply a reaction force.

When in use, the pull wire 152 is attached to groove 7 of a dental bracket 1. This dental bracket 1 is bonded to the tooth 5. When the pull wire 152 is attached, the spring 180 is compressed so that the heating element 130 moves relative to the pull wire 152. After the pull wire 152 is attached, the heating element 130 is allowed to slip into the archwire slot 2 of the dental bracket 1. The trigger 150 is then squeezed by the operator. This causes the spring 170 to expand and the spring 155 to be compressed. Ultimately, the control switch 126 is closed such that the electrical line 128 connected to a power source supplies energy to the heating element 130 at its slotted end 132.

Heating loosens the dental bracket 1 at its adhesive surface 6. A pulling force is applied by means of spring 170 through the sliding block 160 to the pull wire 152. Ultimately, this pulling force will overcome the loosened bonding strength of the adhesive surface 6. At this point, the pull wire 152 removes the dental bracket 1 from the tooth 5. The reaction force supplied by the nose portion allows the bracket 1 to be released and the forces on the spring 1 to be relaxed.

While the preferred embodiments of the invention have been described above, it will be recognized and understood that various modifications may be made therein, and that the appended claims are intended to cover all such modifications and their equivalents which fall within the spirit and scope of the invention.

Having described the invention with the particularity set forth above, what is claimed is:

1. A device for removing a dental bracket having a tie wing and archwire slot extending from a face attached to a tooth comprising:
   a heating element for emplacement in the archwire slot of said bracket;
   pulling means attached to said heating element, said pulling means capable of attachment to the tie wing of a dental bracket;
   a body portion resiliently connected by spring means to said heating element and said pulling means;
   a nose portion attached to said body portion and enclosing said pulling means and said heating element, such that said pulling means and said heating element, such that said pulling means and said heating element are retractable into said nose portion; and
   switch means capable of activating said heating element, said switch means connected to said body portion and operable during the motion of said heating element into the archwire slot of said bracket, such that when said pulling means are attached to said dental bracket, said spring means exert a regulable force on said pulling means which is transferred to said dental bracket.

2. The device of claim 1 wherein said pulling means comprises a pull wire capable of being strung within the space created between the tie wing and face of said dental bracket.

3. The device of claim 2 wherein said heating element is generally cylindrical, with a generally slotted end, said heating element further attached to an external power source and capable of heating said dental bracket by means of resistance heating.

4. The device of claim 3 wherein said body portion is generally cylindrical and contains a generally hollow center, said spring means attached to said body portion such that it is able to expand and contract within said hollow center, said heating element attached to said spring means within said hollow center.

5. The device of claim 4 wherein said spring means are connected to said body portion through a ramp slidable within said hollow center, such that said ramp is capable of loading said spring means, said ramp further connected to said switch means such that when said ramp is moved within said hollow center to load said spring means, said ramp simultaneously activates said switch means.

6. The device of claim 5 wherein said ramp is operable by means of a tab, said tab hinged to the cylindrical wall of said body portion, said tab exposed outside said body portion through a cut-out section of said body portion, such that said tab contacts said ramp to force the sliding of said ramp within said hollow center.

7. The device of claim 2 wherein said nose portion is generally cylindrical and contains a double pronged face capable of emplacement against the tooth onto which the dental bracket is to be removed.

8. A device for removing a dental bracket having a face attached to said tooth, said face supporting a pair of tie wings around an archwire comprising:
   a generally cylindrical heating element having a slotted end adapted to fit within the archwire slot of said dental bracket, said heating element connected to a power source by a control switch;
   a generally cylindrical body section including a generally hollow tube, said control switch connected to said body section, said heating element slidable within said hollow tube such that said control switch activates said heating element upon the sliding of said heating element within said hollow tube;
   first spring means connecting said body section and said heating element;
   a puller assembly attached to said heating element near said heating element slotted end, said puller assembly including a pull wire capable of attachment to the tie wing of a dental bracket by the movement of said pull wire relative to said heating element; and
   a nose portion rigidly attached to said body portion, said nose portion having a generally hollow tubular center for the sliding of said heating element and said puller assembly and providing a base for said device inside the mouth.

9. The device of claim 8 wherein said generally cylindrical body section contains a opening adapted for a finger control, said finger control hinged to said body section and insertable within said hollow tube, said finger control contacting a ramp within said hollow tube, said ramp slidable within said hollow tube and providing attachment means for said first spring means between said heating element and said body portion.

10. The device of claim 9 wherein said first spring means are compressed upon the sliding of said ramp in said hollow tube, said compression capable of exerting a pulling force on said dental bracket when said pull wire is attached to said dental bracket.

11. The device of claim 10 wherein said pull wire is strung behind said tie wings for attachment to said dental bracket.

12. The device of claim 11 including second spring means, said second spring means attached to said ramp and said control switch, such that when said ramp causes the compression of said first spring means, there is a simultaneous compression of said second spring means by said ramp to activate said control switch.

13. The device of claim 12 wherein said nose portion comprises a plurality of prongs having generally flat faces, said prongs capable of straddling said bracket on the face of the tooth upon which said bracket is to be removed.

14. A method for the removal of a dental bracket adhered to a tooth comprising:
   heating said dental bracket;
   simultaneously pulling said dental bracket with a regulated force to overcome the bonding strength of the loosened heated adhesive; and
   creating a reaction force near said dental bracket, such that the tooth to which said bracket is adhered is not pulled.

15. A method for the removal of a dental bracket having a tie wing and an archwire slot comprising:
   attaching a pull wire to said tie wing, said pull wire resiliently connected to a heating element; inserting said heating element in the archwire slot of said bracket;
   activating a switch means connected to said heating element to initiate heating said bracket upon the insertion of said element within said archwire slot;
   providing a pulling force to said pull wire, said pulling force regulated by spring means connected to said pull wire;
   providing a reaction force to the mouth near said dental bracket; and
   heating said bracket until the pulling force overcomes the adhesive force bonding said bracket to said tooth.

* * * * *